United States Patent [19]

Roman

[11] 3,962,233
[45] June 8, 1976

[54] 2-(HALONITRO(ORGANOOXYCARBONYL)-METHYL)-5,6-DIHYDRO-4H-1,3-THIAZINES

[75] Inventor: Steven A. Roman, Oakdale, Calif.
[73] Assignee: Shell Oil Company, Houston, Tex.
[22] Filed: Feb. 19, 1975
[21] Appl. No.: 551,171

Related U.S. Application Data

[63] Continuation-in-part of Ser. No. 468,123, May 8, 1974, abandoned.

[52] U.S. Cl................... 260/243 R; 424/246
[51] Int. Cl.² ........................... C07D 279/06
[58] Field of Search ...................... 260/243 R

[56] References Cited
OTHER PUBLICATIONS

Hirai, et al., *Chem. Pharm. Bull.*, vol. 20, pp. 97–101 (1972).

*Primary Examiner*—John M. Ford

[57] ABSTRACT

Novel insecticidal 2-(halonitro(organooxycarbonyl)-methyl)-5,6-dihydro-4H-1,3-thiazines.

1 Claim, No Drawings

2-(HALONITRO(ORGANOOXYCARBONYL)METHYL)-5,6-DIHYDRO-4H-1,3-THIAZINES

This application is a continuation-in-part of application Ser. No. 468,123, filed May 8, 1974, now abandoned.

DESCRIPTION OF THE INVENTION

It has been found that useful insecticidal activity is possessed by certain 5,6-dihydro-4H-1,3-thiazines substituted at the carbon atom in the 2-position by a carbon atom bonded to nitro, to halogen and to an organooxycarbonyl moiety. These compounds can be described by the formula

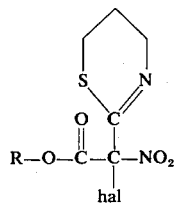

wherein "hal" is halogen selected from chlorine, bromine and fluorine, and R contains up to 30 carbon atoms and is alkyl, alkenyl, alkynyl, cycloalkyl, cycloalkylalkyl, haloalkyl, haloalkenyl, mono- and poly-(alkoxy)alkyl, alkylthioalkyl, phenylthioalkyl, benzylthioalkyl, cyanoalkyl, hydroxyalkyl, alkylsulfinylalkyl, aryl or aralkyl or either substituted on the ring by one to two of one or more of halogen, nitro, cyano, alkyl, aryl, alkoxy or aryloxy; is aminoalkyl, $-(CH_2)_{\overline{m}}NR^3R^4$, wherein $m$ is one or two, $R^3$ is alkyl, cycloalkyl, alkenyl, aryl or aralkyl, and $R^4$ is hydrogen or one of the moieties represented by $R^3$; or is $-(CH_2)_{\overline{n}}R^5$, wherein $n$ is zero, one or two, and $R^5$ is a heteromonocyclic moiety of from five to six carbon atoms in the ring, containing in the ring carbon atoms and one to two of oxygen (—O—), sulfur (—S—) and nitrogen (—N— or —NH—) bonded to carbon in the ring.

Preferably, the moiety represented by R contains no more than ten carbon atoms and when aliphatic may be of straight-chain or branched-chain configuration. The preferred aryl moieties are optionally substituted phenyl. The preferred aminoalkyl moieties are dialkylaminomethyl and -ethyl. The preferred aralkyl moieties are optionally-substituted phenylmethyl. Preferred heterocyclic ($R^5$) moieties are furanyl, tetrahydrofuranyl, dioxolanyl, thienyl, thiopyranyl, pyridinyl, pyrrolidinyl, morpholinyl, and their $R^5$-methyl- counterparts.

The compounds of this invention may be described as esters of alpha-halo-alpha-nitro-5,6-dihydro-4H-1,3-thiazine-2-acetic acid.

For illustration, preparation of typical species of this genus of compounds is described in the examples included hereinafter. Other typical, illustrative species of this genus are those wherein the symbols represent the following moieties, this manner of naming these species being accurate, yet pointing out the differences between the different species more clearly than if the entire complicated name of each species were to be given:

hal = Br, R = (tetrahydro-2-furanyl)methyl
3-chloropropyl
4-chlorobenzyl
2-propynyl
2,2,2-trifluoroethyl
cyclopentyl
2-methoxyethyl
tetrahydro-2-furanyl
1-naphthalenylmethyl
3-phenoxybenzyl
2,4-dichlorobenzyl
2-methylthioethyl
isobornyl
2-(dimethylamino)ethyl
tetrahydro-2H-thiopyran-2-yl
2-pyridinylmethyl
2-(4-morpholinyl)ethyl
2-methylsulfinylethyl
phenyl
2-cyanopropyl
farnesyl
2-(diphenylamino)ethyl
(1-methyl-2-piperidinyl)methyl
2-imidazolylmethyl
2-pyrimidinylmethyl
benzylideneaminomethyl hal = Cl, R = 2-(methylthio)ethyl
2-thienylmethyl
2-pyridylmethyl
3-chloro-2-propenyl
allyl
2-butenyl
2-methoxyethyl
2-furanylmethyl
2-butynyl
2-(2-methoxyethoxy)ethyl
4-cyanobenzyl
(cis) and (trans) 3-chloro-2-propenyl
2-thienylmethyl
cyclohexylmethyl
menthyl
2-hydroxyethyl
norbornyl
2-(phenylthio)ethyl
benzyl
cholesteryl
(1-methyl-2-pyrrolyl)methyl
2-thiazolylmethyl
2-oxazolylmethyl
2-(1-pyrrolidinyl)ethyl
2-quinolinylethyl
1-methyl-3-piperidinyl
2-piperidinylmethyl
2-imidazolylmethyl
2-(methylamino)ethyl
2-(benzylthio)ethyl
(diallylamino)methyl
3-phenoxybenzyl hal = F, R = methyl
cyclopropylmethyl Generally, the compounds of this invention in which "hal" is chlorine or bromine are readily prepared by treating a nitro(tetrahydro-2H-1,3-thiazine-2-ylidene)acetic acid ester with a halogen or a halogenating agent containing positive chlorine or bromine such as N-chloro- or N-bromosuccinimide or tert-butyl hypochlorite, at about room temperature or below in a haloalkane as solvent or liquid reaction medium. Compounds of this invention wherein "hal" is fluorine can be prepared by treating the ester with conventional fluorinating agents (cf. Noller, "Chemistry of Organic Compounds," 3rd Edition, 1965, at pages 801 et seq.). A convenient method is to employ perchloryl fluoride as the fluorinating agent. Conditions for the treatment are as for use of the positive chlorinating and brominating agents.

The precursor esters can be prepared in a number of ways. The most facile method for preparing them appears to be the base-promoted transesterification of the methyl or ethyl ester. These esters can be prepared by the zinc ion-catalyzed reaction of 5,6-dihydro-2-(methylthio)-4H-1,3-thiazine (A. F. McKay et al., J. Am. Chem. Soc. 80, 3339 (1950)) with methyl or ethyl nitroacetate (S. Zen et al, Kogyo Kagaku Zasshi, 74, 70 (1971)).

This procedure also can be used to prepare other esters from the appropriate ester of nitroacetic acid.

The ester interchange follows the conventional base catalyzed reaction of an ester with the alcoholate of the appropriate alcohol. According to one technique, the interchange can be affected by treating the alkyl ester with an excess of the appropriate alcohol in the presence of two equivalents of an alkali metal (one equivalent of the metal converts the alcohol to the alcoholate, while the other equivalent neutralizes the acidic thiazine ester products). Use of a small to moderate (5–10 percent) excess of the metal may be desirable in some cases. Generally, the reaction can be effected at temperatures of about 20°–100°.

Alternatively, the metal alcoholate can be prepared and reacted with the ester in an aprotic low-dielectric solvent, such as tetrahydrofuran. This may be done by treating the appropriate alcohol in the solvent with an alkali metal hydride, then adding the ester, also in the solvent. The reaction of the alcohol and hydride usually is exothermic so that cooling is usually needed to control the temperature of the reaction mixture. Reaction of the alcoholate with the ester ordinarily can be conducted at room temperature. With either technique, recovery of the product is most effectively attained in most cases by quenching the final reaction mixture in water, treating the aqueous mixture with a suitable solvent such as ether to remove the solvent alcohol and other neutral organic species, then acidifying the aqueous phase. In some cases, the product ester crystallizes out of the water; in other cases, it can be recovered by extracting the water-phase with a suitable water insoluble solvent such as methylene chloride.

The esters, all of which are suitable precursors for compounds of this invention, are the subject of Ser. No. 468,125 filed May 8, 1974, now abandoned, the pertinent portions thereof being incorporated herein to illustrate preparation of such esters.

These procedures for preparing compounds of this invention are illustrated in the following examples. In all cases, the identity of the product, and of any intermediate employed, was confirmed by elemental analysis and by infrared and nuclear magnetic resonance spectrum analyses.

EXAMPLE 1

Methyl alpha-bromo-5,6-dihydro-alpha-nitro-4H-1,3-thiazine-2-acetate (1)

a. Preparation of methyl nitro)tetrahydro 2H-1,3-thiazin-2-ylidine)acetate (1a)

To a mixture of 221 g of 5,6-dihydro-2-(methylthio)-4H-1,3-thiazine and 1 g of zinc chloride at 100°, 202 g of methyl nitroacetate was added dropwise over a 30-minute period. The resulting mixture was heated for 4 hours at 95°–105°. Then, 100 ml of isopropyl alcohol was added to the hot mixture, then 400 ml of ether was added. The mixture was filtered to give 1a, m.p.: 107°–108°.

b. Preparation of (1).

10.9 g of 1a, 8.2 g of N-bromosuccinimide and 250 ml of carbon tetrachloride were mixed at room temperature and the mixture allowed to stand at room temperature for 18 hours. The mixture then was filtered and the solvent stripped from the filtrate under vacuum to leave an oil which crystallized on standing to give a pale yellow solid, m.p.: 88.5°–93°. This solid was recrystallized from ether/hexane to give 1 as a white solid, m.p.: 95°–95.5°.

EXAMPLES 2–8

In the manner described in Example 1, the following additional species were prepared by treatment of the appropriate esters with N-chloro- or N-bromosuccinimide.

Methyl alpha-chloro-5,6-dihydro-alpha-nitro-4H-1,3-thiazine-2-acetate (2) as a white solid, m.p.: 61°–63°.

2-methylpropyl alpha-bromo-5,6-dihydro-alpha-nitro-4H-1,3-thiazine-2-acetate (3) as a solid, m.p.: 53.5°–54°.

1-methylethyl alpha-bromo-5,6-dihydro-alpha-nitro-4H-1,3-thiazine acetate (4) as a solid, m.p.: 99°–100°.

2-methylpropyl alpha-chloro-5,6-dihydro-alpha-nitro-4H-1,3-thiazine acetate (5) as a yellow oil.

Octyl alpha-bromo-5,6-dihydro-alpha-nitro-4H-1,3-thiazine acetate (6) as a solid, m.p.: 32°–33°.

Cyclopropylmethyl alpha-chloro-5,6-dihydro-alpha-nitro-4H-1,3-thiazine acetate (7) as a white solid, m.p.: 53.5°–54°.

(4-methoxyphenyl)methyl alpha-chloro-5,6-dihydro-alpha-nitro-4H-1,3-thiazine acetate (8), as a yellow solid, m.p.: not determined.

Compounds of this invention exhibit useful insecticidal activity, being of particular interest for control of the larvae "caterpillar" or "worm" forms of insects of the genus Heliothis, such as $H.$ $zea$ (corn earworm, cotton bollworm, tomato fruitworm), $H.$ $virescens$ (tobacco budworm); the genus Agrotis, such as $A.$ $ipsilon$ (black cutworm); the genus Trichoplusia, such as $T.$ $ni$ (cabbage looper), and the genus Spodoptera, such as $S.$ $littoralis$ (Egyptian cotton leafworm). Some are also of interest for controlling whiteflies and houseflies. In tests that have been conducted they have exhibited low, or no, toxicity to other insects such as the 2-spotted spider mite and mosquito larva. Some act very rapidly providing "quick knock-down" of insects; in some cases even though the compound is not very toxic to the insects.

Activity of compounds of this invention with respect to insects was determined by using standardized test methods to establish the $LC_{50}$ dosage (in milligrams of test compound per 100 milliliters of solvent or liquid carrier required in the solution or suspension of test compound used) to kill 50 percent of the test insects. The test insects were the housefly, corn earworm, mosquito, pea aphid and 2-spotted spider mite, and in one case the black cutworm.

All of compounds 1 through 8 were active with respect to the corn earworm. Compounds 1, 3, 4, 5 and 8 were active with respect to the housefly. Compounds 1–4, 6 and 8 were active with respect to the pea aphid. Compound 1 was tested and found active with respect to the black cutworm.

In the course of these tests it was noted that compounds 1 and 4 acted very quickly on houseflies, and compounds 1 through 8 acted very quickly upon corn earworms.

The invention includes within its scope insecticidal compositions comprising an adjuvant — that is, a carrier, optionally a surface-active agent — and, as active ingredient, at least one insecticide of this invention.

Likewise the invention includes also a method of combatting insect pests at a locus which comprises applying to the locus an effective amount of at least one insecticide of the invention.

The term "carrier" as used herein means a material, which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols, bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001 to 0.5 percent based on the total weight of the formulation, though under some circumstances the effective concentration will be as little as 0.0001 or as much as 2 percent, on the same basis.

I claim as my invention:

1. A 2-(halonitro(organooxycarbonyl)methyl)-5,6-dihydro-4H-1,3-thiazine of the formula

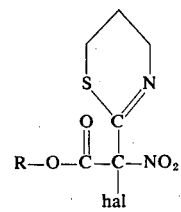

wherein "hal" is halogen selected from chlorine, bromine and fluorine, and R contains up to thirty carbon atoms and is alkyl, alkenyl, alkynyl, cycloalkyl, cycloalkylalkyl, haloalkyl, haloalkenyl, mono- and poly(alkoxy)alkyl, alkylthioalkyl, phenylthioalkyl, benzylthioalkyl, cyanoalkyl, hydroxyalkyl, alkylsulfinylalkyl, phenyl or phenalkyl or either substituted on the ring by one to two of one or more of halogen, nitro, cyano, alkyl, phenyl, alkoxy or phenoxy; is aminoalkyl, $(CH_2)_m NR^3R^4$, wherein $m$ is one or two, $R^3$ is alkyl, cycloalkyl, alkenyl, phenyl or phenalkyl, and $R^4$ is hydrogen or one of the moieties represented by $R^3$; or is $(CH_2)_n R^5$, wherein $n$ is zero, one or two, and $R^5$ is a heteromonocyclic moiety of from five to six carbon atoms in the ring, containing in the ring carbon atoms and one to two of oxygen (—O—), sulfur (—S—) and nitrogen (—N— or —NH—) bonded to carbon in the ring.

* * * * *